(12) United States Patent
Kashiwagi et al.

(10) Patent No.: US 6,448,452 B2
(45) Date of Patent: Sep. 10, 2002

(54) FLUORINE-CONTAINING DIENE, ITS PRODUCTION METHOD AND ITS POLYMER

(75) Inventors: Kimiaki Kashiwagi; Hidenobu Murofushi; Norihide Sugiyama; Masakuni Sato; Atsushi Watakabe, all of Kanagawa (JP)

(73) Assignee: Asahi Glass Company Limited, Tokyo (JP)

( * ) Notice: Subject to any disclaimer, the term of this patent is extended or adjusted under 35 U.S.C. 154(b) by 0 days.

(21) Appl. No.: 09/841,592

(22) Filed: Apr. 25, 2001

(30) Foreign Application Priority Data

Apr. 26, 2000 (JP) .......................... 2000-125615

(51) Int. Cl.⁷ .................... C07C 41/00; C07C 43/00; C07C 17/02; C07C 19/08; C07C 17/266; C07C 11/00; C07C 2/02

(52) U.S. Cl. .................. 568/683; 568/685; 570/125; 570/128; 570/138; 570/142; 570/172; 585/18; 585/502; 585/507

(58) Field of Search .................... 585/18, 502, 507; 570/125, 128, 138, 142, 172; 568/683, 685; 106/901; 526/247

(56) References Cited

U.S. PATENT DOCUMENTS 5,260,492 A * 11/1993 Feiring et al.
5,350,821 A    9/1994 Feiring et al.
5,502,132 A    3/1996 Sugiyama et al.

FOREIGN PATENT DOCUMENTS

JP   02 311436   12/1990

* cited by examiner

*Primary Examiner*—Sreeni Padmanabhan
*Assistant Examiner*—Sikarl A. Witherspoon
(74) *Attorney, Agent, or Firm*—Oblon, Spivak, McClelland, Maier & Neustadt, P.C.

(57) ABSTRACT

A polymer which contains monomer units formed by polymerization of a fluorine-containing diene of formula 1:

$$CF_2=CF(CF_2)_nCXYOCF=CF_2$$

Wherein X and Y are hydrogen and chlorine, hydrogen and bromine, hydrogen and iodine, fluorine and chlorine, fluorine and bromine, fluorine and iodine, chlorine and bromine, chlorine and iodine, bromine and bromine, bromine and iodine, or iodine and iodine and n is an integer from 1 to 3.

8 Claims, No Drawings

FLUORINE-CONTAINING DIENE, ITS PRODUCTION METHOD AND ITS POLYMER

The present invention relates to a fluorine-containing diene having two unsaturated bonds, its production method and its polymer.

As a fluorine-containing diene having two carbon-carbon unsaturated double bonds (hereinafter referred to as unsaturated bonds), $CF_2=CF(CF_2)_kOCF=CF_2$ (wherein k is an integer of from 1 to 3) has been known (JP-A-1-14843). By cyclic polymerization of this compound, an amorphous polymer can be obtained, which has high elastic modulus, yield elongation in tension and breaking extension, which is less likely to break and is excellent in impact resistance. It also has a high transparency, and it can thereby be used as a material for optical components or optical devices such as optical waveguides or optical fibers. However, in a case where an optical resin material is obtained by using this polymer, since the polymer has a low glass transition temperature, the optical properties tend to change by a long-term use at a high temperature.

It is an object of the present invention to provide a polymer which maintains mechanical properties of the above amorphous polymer and has a higher glass transition temperature, and can thereby be an optical resin material excellent in heat resistance, and a fluorine-containing diene having two unsaturated bonds to give such a polymer.

The present invention provides a fluorine-containing diene represented by the following formula 1, its production method and its polymer, a fluorine-containing compound represented by the following formula 2, a method of producing the fluorine-containing diene represented by the following formula 1, which comprises dehalogenating the fluorine-containing compound represented by the formula 2, and a polymer which contains a polymer formed by polymerization of the fluorine-containing diene represented by the formula 1 in monomer units:

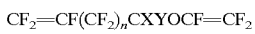    Formula 1

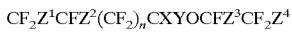    Formula 2 wherein each of X and Y which are independent of each other, is an atom selected from a hydrogen atom, a fluorine atom, a chlorine atom, a bromine atom and an iodine atom, provided that X and Y are neither simultaneously hydrogen atoms nor simultaneously fluorine atoms, each of $Z^1$, $Z^2$, $Z^3$ and $Z^4$ which are independent of one another, is a halogen atom selected from a chlorine atom, a bromine atom and an iodine atom, and n is an integer of from 1 to 3.

With respect to X and Y in the formulae 1 and 2, preferably at least one is a chlorine atom, particularly preferably both are chlorine atoms or one is a chlorine atom and the other is a fluorine atom. Particularly preferably, one is a chlorine atom and the other is a fluorine atom. Further, with respect to $Z^1$, $Z^2$, $Z^3$ and $Z^4$, preferably at least one is a chlorine atom, particularly preferably all are chlorine atoms. A chlorine atom strongly connects with a carbon atom as compared with a bromine atom and an iodine atom, such being favorable in view of stability of a compound, and in synthesis of the compound of the present invention and in polymerization of the fluorine-containing diene represented by the formula 1, a reaction such as release of a halogen atom is less likely to take place. Further, the desired dehalogenation reaction can easily be carried out as compared with a case of a fluorine atom or a hydrogen atom. Here, the carbon atom to which X and Y are bonded, is adjacent to an oxygen atom and a difluoromethylene group, whereby a dehalogenation reaction hardly takes place, and the stability is high even if X or Y is a chlorine atom.

The fluorine-containing compound represented by the formula 2 (hereinafter sometimes referred to as a fluorine compound (2)), wherein each of X, Y, $Z^1$, $Z^2$, $Z^3$ and $Z^4$ is a chlorine atom, can be produced, for example, by the following method. Namely, iodine chloride and trifluorochloroethylene are reacted at a low temperature to produce a compound (a) represented by the formula 3, which is reacted with a predetermined amount of tetrafluoroethylene in the presence of a radical initiator to produce a compound (b) represented by the formula 4, which is oxidized by fuming sulfuric acid to obtain a compound (c) represented by the formula 5, followed by alkylesterification to produce a compound (d) represented by the formula 6 (wherein R is an alkyl group).

The compound (d) is reduced by e.g. sodium borohydride to produce a compound (e) represented by the formula 7, then this compound (e) is reacted with a metal hydride, and the resulting metal alkoxide is reacted with tetrafluoroethylene to produce a compound (f) represented by the formula 8. The compound (f) is chlorinated so that every hydrogen atom in the compound (f) is replaced by a chlorine atom, and chlorine atoms are added to the unsaturated bond to obtain the desired fluorine-containing compound represented by the formula 9 i.e. the fluorine-containing compound represented by the formula 2, wherein each of X, Y, $Z^1$, $Z^2$, $Z^3$ and $Z^4$ is a chlorine atom (hereinafter referred to as a compound (g)). Here, in this method, by making tetrafluoroethylene react with the compound (a) to produce the compound (b), the desired compound wherein n is 1 or 3 can be obtained. The desired compound wherein n is 2 can be obtained by another known method to produce the compound represented by the formula 5 wherein n is 2, and then conducting the same operation as mentioned above.

    Formula 3

    Formula 4

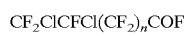    Formula 5

    Formula 6

    Formula 7

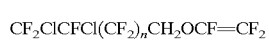    Formula 8

    Formula 9

Further, by changing conditions of the chlorination in the chlorination step to obtain the compound (g), the chlorine-containing compound represented by the formula 2, wherein X is a hydrogen atom, Y is a chlorine atom, and each of $Z^1$, $Z^2$ $Z^3$ and $Z^4$ is a chlorine atom (a compound represented by the following formula 10), can be produced. For example, by partial chlorination by adjusting the feed amount of a chlorine gas or the ultraviolet irradiation intensity in the chlorination step as mentioned hereinafter, one of the two hydrogen atoms in the compound (f) can be replaced by a chlorine atom. Further, by partial fluorination of the compound (g) represented by the formula 9, the fluorine-containing compound represented by the formula 2, wherein X is a fluorine atom, Y is a chlorine atom and each of $Z^1$, $Z^2$, $Z^3$ and $Z^4$ is a chlorine atom (a compound represented by the following formula 11, hereinafter sometimes referred to as a compound (h)) can be produced.

CF$_2$ClCFCl(CF$_2$)$_n$CHClOCFClCF$_2$Cl            Formula 10

CF$_2$ClCFCl(CF$_2$)$_n$CFClOCFClCF$_2$Cl            Formula 11

By the reaction of iodine chloride and trifluorochloroethylene is carried out by a method disclosed in a literature (*J. Am. Chem. Soc.*, 83, 2495 (1981)) at a low temperature, preferably from −8° C. to 0° C., the compound (a) is selectively formed. The reaction of the compound (a) and tetrafluoroethylene is carried out in the presence of a radical initiator such as a peroxide or an azo compound, usually at from 20 to 150° C., preferably from 60 to 100° C., while keeping tetrafluoroethylene under at most 1 MPa, preferably at most 0.5 MPa, to obtain the compound (b).

The production of the compound (c) by oxidation of the compound (b) is carried out, for example, by fuming sulfuric acid. The concentration of fuming sulfuric acid may optionally be selected. The reaction temperature varies depending upon the concentration of the fuming sulfuric acid, but is from 40 to 100° C., preferably from 60 to 80° C., when the concentration is 60 mass %, for example. The alkylesterification of the compound (c) is carried out by dropwise adding the compound (c) to an alkanol, for example. By reacting an alkanol with the compound (c) at a low temperature, preferably at from 0° C. to 20° C., the corresponding compound (d) can be obtained. As the alkanol, preferred is an alkanol having a carbon number of at most 4. The reduction reaction of the compound (d) is carried out, for example, by sodium borohydride or lithium aluminum hydride. The reaction is carried out at a low temperature, preferably from 0° C. to 20° C. to obtain the compound (e) as the corresponding fluorine-containing alcohol.

With the compound (e), a metal hydride such as sodium hydride or lithium hydride is reacted at a low temperature, preferably at from 0° C. to 20° C., to produce a fluorine-containing alkoxide corresponding to the compound (e). As the metal atom in the fluorine-containing alkoxide, in addition to sodium or lithium, an alkali metal atom such as potassium or cesium, or a silver atom, may, for example, be mentioned. As a reaction solvent, a non-cyclic or cyclic ether type solvent or an aprotic polar solvent may be used. Specifically, diethyl ether, methyl tert-butyl ether, tetrahydrofuran, 1,4-dioxane, monoglyme, diglyme, triglyme, tetraglyme, acetonitrile, benzonitrile, sulfolane, dimethylacetamide or dimethylsulfoxide may, for example, be used.

The formed fluorine-containing alkoxide is moved to an autoclave together with the reaction solvent without isolation, tetrafluoroethylene is introduced thereto at a temperature of from −10 to +50° C., preferably from 0 to +30° C., until the pressure becomes from 0.5 to 3.5 MPa, preferably from 1 to 2 MPa, and the reaction temperature is raised to a temperature of from 30 to 100° C., preferably from 50 to 60° C., so that the fluorine-containing alkoxide and tetrafluoroethylene are reacted to form the compound (f). The reaction time is from 30 minutes to 120 hours, preferably from about 10 hours to about 30 hours.

Then, the compound (f) is chlorinated so as to replace the two hydrogen atoms in the methylene group by chlorine atoms and to add chlorine atoms to the unsaturated group. As this chlorination, thermal chlorination or photo-chlorination is suitable, and particularly as the replacement by chlorine, photo-chlorination is preferred. Both replacement by chlorination and chlorine-addition reaction may be carried out by photo-chlorination. For example, it is carried out by passing chlorine gas through the solution of the compound (f) under irradiation with ultraviolet light. At the beginning of the reaction, chlorine addition to the unsaturated bond takes place, and as this reaction involves heat generation, it is preferred to carry out the reaction while cooling the system. The reaction temperature is suitably from 0 to 100° C., and it is preferred to conduct the reaction by adjusting the temperature to be from 20 to 40° C. The addition reaction is followed by a replacement of the methylene group by chlorine. This replacement reaction is usually carried out under irradiation with ultraviolet light at a reaction temperature higher than the above temperature, and the reaction temperature is suitably from 40 to 200° C., preferably from 60 to 120° C. By carrying out such a chlorination reaction, the compound (g) can be obtained. By adjusting the reaction conditions of the latter photo-chlorination reaction, partial chlorination of the methylene group can be achieved.

By partial fluorination of the dichloromethylene group adjacent to the ethereal oxygen atom in the compound (g) to replace only one chlorine atom by a fluorine atom (Macromolcules, 26, 5829 (1993) or U.S. Pat. No. 4,594, 399), the compound (h) can be obtained. This partial fluorination can be carried out by treating the compound (g) with a mixture of antimony trifluoride and antimony pentachloride. This reaction can be carried out without a solvent, or can be carried out in an inert solvent such as a perfluorohydrocarbone solvent. The reaction temperature is suitably from 50 to 200° C., preferably from 80 to 120° C. One of the two chlorine atoms in the dichloromethylene group is easily replaced by a fluorine atom as compared with a chlorine atom in a chlorofluoromethylene group. The chlorofluoromethylene group after the replacement by a fluorine atom is less likely to further be fluorinated by the above fluorination method, similar to other chlorofluoromethylene groups.

By dehalogenation of the fluorine-containing compound (2), the fluorine-containing diene represented by the formula 1 can be obtained. In this case, even when X or Y in the fluorine-containing compound (2) is a halogen atom, no dehalogenation takes place under usual dehalogenation reaction conditions. This is attributable to the fact that the carbon atom adjacent thereto have no halogen atom of the same type. As a result, $Z^1$ and $Z^2$, and $Z^3$ and $Z^4$, undergo dehalogenation to produce two double bonds. This dehalogenation is carried out preferably in a polar solvent by using a dehalogenating agent.

The dehalogenating agent is a reaction agent acting on a halogen atom in a substrate and taking the halogen atom off. As the dehalogenating agent, preferred is zinc, sodium, magnetism, tin, copper, iron or another metal. As the dehalogenating agent, preferred is zinc from the viewpoint of reaction conditions such that a relatively low reaction temperature can be employed. As the polar solvent, an organic polar solvent such as dimethylformamide, dimethylacetamide, N-methylpyrrolidone, 1,4-dioxane, diglyme or methanol, or water, may, for example, be used preferably. Further, the molar ratio of the dehalogenating agent relative to the fluorine-containing compound (2) is suitably from 2 to 10 times, preferably from 5 to 8 times. The reaction temperature is suitably from 40 to 100° C., preferably from 50 to 60° C. The reaction is carried out usually by dropwise adding the fluorine-containing compound (2) in the presence of the dehalogenating agent and the solvent, and isolation of the reaction product is carried out by taking the reaction product off from the reaction system immediately after the reaction by distillation.

The fluorine-containing diene represented by the formula 1 of the present invention is polymerizable and is useful as a monomer for producing a fluorine-containing polymer. This fluorine-containing diene undergoes cyclic polymerization by the effect of a radical polymerization initiator to form a polymer having monomer units having a fluorine-containing alicyclic structure. Further, it can be copolymerized with another monomer. The another monomer copolymerizable with the fluorine-containing diene is not particularly limited so long as it is a radical-polymerizable monomer, and examples of which include a fluorine-containing monomer, a hydrocarbon type monomer and other monomers. Particularly preferred is an olefin such as ethylene or a fluoroolefin such as tetrafluoroethylene, chlorotrifluoroethylene or vinylidene fluoride. Further, the fluorine-containing diene may be copolymerized with a fluorine-containing vinyl ether type monomer such as perfluoro(alkyl vinyl ether), a fluorine-containing diene which may undergo cyclic polymerization (other than the compound represented by the formula 1) such as perfluoro (butenyl vinyl ether) or perfluoro(allyl vinyl ether), or a monomer having a fluorine-containing alicyclic structure such as perfluoro(2,2-dimethyl-1,3-dioxole) or perfluoro(2-methylene-4-methyl-1,3-dioxolane). These monomers may be used alone or in combination of at least two for copolymerization with the fluorine-containing diene.

The present invention further provides a homopolymer of the above fluorine-containing diene of the present invention, a copolymer of at least two types thereof, and a copolymer of the above fluorine-containing diene of the present invention with another monomer copolymerizable therewith. The proportion of the monomer units formed by polymerization of the fluorine-containing diene of the present invention in the polymer is preferably from 30 to 100 mol %, particularly preferably from 50 to 100 mol %, based on the total monomer units. Further, the molecular weight is preferably from 500 to 100,000, particularly preferably from 500 to 10,000.

As the radical polymerization initiator, a polymerization initiator which is used for an usual radical polymerization, such as an azo compound, an organic peroxide or an inorganic peroxide, may be used. Specific examples of the radical polymerization initiator include azo compounds such as diisopropyl peroxydicarbonate, 2,2'-azobis(2-amidinopropane)dihydrochloride, 4,4'-azobis(4-cyanopentanoic acid), 2,2'-azobis(4-methoxy-2,4-dimethylvaleronitrile) and 1,1'-azobis(1-cyclohexanecarbonitrile), organic peroxides such as benzoyl peroxide, perfluorobenzoyl peroxide, perfluorononanoyl peroxide, methyl ethyl ketone peroxide and diisopropyl peroxydicarbonate, and inorganic peroxides such as $K_2S_2O_8$ and $(NH_4)_2S_2O_8$.

The polymerization method is not particularly limited also, and a so-called bulk polymerization of directly supplying the fluorine-containing diene to polymerization, a solution polymerization employing an organic solvent dissolving the fluorine-containing diene, such as a fluorinated hydrocarbon, a chlorinated hydrocarbon, a chlorinated fluorinated hydrocarbon, an alcohol or a hydrocarbon, a suspension polymerization carried out in an aqueous medium in the presence or absence of a proper organic solvent, or an emulsion polymerization carried out in an aqueous medium in the presence of an emulsifying agent, may, for example, be mentioned. The temperature and the pressure for the polymerization are not particularly limited, but preferably they are optionally set taking various factors such as boiling point of the fluorine-containing diene, the heat source required and removal of polymerization heat into consideration. For example, the polymerization temperature can suitably be set within a range of from 0 to 200° C., and the polymerization is carried out particularly preferably at a temperature of from 30 to 100° C. Further, the polymerization may be carried out under reduced pressure or under elevated pressure, and the polymerization can suitably be carried out under a level of from normal pressure to 10 MPa practically, preferably at a level of from normal pressure to 5 MPa.

The polymer of the present invention is characterized by that it is extremely excellent in transparency, it has a high elastic modulus, yield elongation in tension and breaking extension, it is less likely to break and is excellent in impact resistance, it has a high glass transition temperature and has a high heat resistance. Accordingly, the polymer of the present invention can be used as an optical resin material for optical components or optical devices such as optical fibers, optical waveguides and lenses, excellent in heat resistance by themselves. Further, the polymer of the present invention is characterized also by that it is optically transparent and has a refractive index higher than that of a conventional transparent fluororesin. Accordingly, by combining with e.g. a conventional transparent fluororesin having a low refractive index, high performance optical devices excellent in optical transparency, such as optical fibers or optical waveguides, can be obtained. For example, with respect to the optical fiber as disclosed in JP-A-8-5484, the polymer of the present invention can be used as an amorphous fluorine-containing polymer or as a low-molecular weight polymer (oligomer) to be used together with an amorphous fluorine-containing polymer.

Now, the present invention will be explained in further detail with reference to Examples and Comparative Examples. However, it should be understood that the present invention is by no means restricted to such specific Examples.

EXAMPLE 1

Synthesis of $CF_2ClCFClCF_2CCl_2OCFClCF_2Cl$:
Synthesis of Compound (g) from Compound (f)

Into a 1 l four-necked flask equipped with a stirrer, a dry ice condenser and a UV lamp, 1,100 g (3.51 mol) of $CF_2ClCFClCF_2CH_2OCF=CF_2$ (synthesized by a method as disclosed in U.S. Pat. No. 5,260,492) was charged, the system was cooled, and chlorine gas was blown through the flask under irradiation with ultraviolet light. This reaction proceeded while generating heat, and after completion of chlorine addition to the double bond, heat generation did not take place any longer. Then, the system was heated to from 70 to 100° C., and chlorine gas was blown therethrough under irradiation with ultraviolet light. Supply of chlorine gas was terminated when 1,420 g (20.0 mol) of chlorine gas was introduced, a crude reaction product was recovered, and the crude reaction product was further distilled off to obtain 1,050 g (yield 65%) of pure $CF_2ClCFClCF_2CCl_2OCFClCF_2Cl$ (1,2,4,4,6,7-hexachloro-1,1,2,5,5,6,7,7-octafluoro-3-oxa-heptane).

b.p.: 80° C./0.67 kPa $CF^a_2ClCF^bClCF^c_2CCl_2OCF^dClCF^e_2Cl$; $^{19}F$-NMR (based on $CDCl_3$, $CFCl_3$) δ ppm; −64.2 and −70.8 ($F^a$ and $F^e$, 4F), −79.8 ($F^d$, 1F), −100 to −110 ($F^c$, 2F), −126.1 ($F^b$, 1F).

EXAMPLE 2

Synthesis of $CF_2ClCFClCF_2CFClOCFClCF_2Cl$:
Synthesis of Compound (h) from Compound (g)

Into a 500 ml four-necked flask equipped with a stirrer, a reflux condenser and a dropping funnel, 100 g (0.56 mol) of antimony trifluoride was introduced, and 215 g (0.47 mol) of $CF_2ClCFClCF_2CCl_2OCFClCF_2Cl$ and 16.8 g (0.056 mol) of antimony pentachloride were introduced thereto in an atmosphere of an inert gas. Then, the flask was heated with well stirring until the internal temperature became 110 to 120° C., and the reaction was carried out for 4 hours at that temperature. Then, a remaining solid was removed by filtration, and a crude product was distilled to obtain 130 g (yield: 62%) of pure $CF_2ClCFClCF_2CFClOCFClCF_2Cl$ (1,2,4,6,7-pentachloro-1,1,2,4,5,5,6,7,7-nonafluoro-3-oxa-heptane).

b.p.: 62° C./0.75 kPa $CF^a{}_2ClCF^bClCF^c{}_2CF^dClOCF^eClCF^f{}_2Cl$ $^{19}$F-NMR (based on CDCl$_3$, CFCl$_3$) δ ppm; −64.0 and −70.8 (F$^a$ and F$^f$, 4F), −68.5 to −74.5 (F$^d$, 1F), −78.0 (F$^e$, 1F), −107.2 to −115.2 (F$^c$, 2F), −125 to −132 (F$^b$, 1F).

EXAMPLE 3

Synthesis of $CF_2$=$CFCF_2CCl_2OCF$=$CF_2$:
Synthesis of Compound (h) from Compound (g)

Into a 500 ml four-necked flask equipped with a stirrer, a reflux condenser and a dropping funnel, 115 g (1.77 mol) of zinc was introduced, and 200 ml of dimethylformamide was introduced thereinto in an atmosphere of an inert gas. Then, the pressure in the system was reduced to 3 kPa, and the internal temperature was adjusted to from 50 to 55° C., and 100 g (0.22 mol) of $CF_2ClCFClCF_2CCl_2OCFClCF_2Cl$ was dropwise added thereto gradually by the dropping funnel, and the resulting product was quickly taken out by distillation during the reaction. Then, the crude product was purified to obtain 42 g (yield 62%) of pure $CF_2$=$CFCF_2CCl_2OCF$=$CF_2$ (4,4-dichloro-1,1,2,5,5,6,7,7-octafluoro-3-oxa-1,6-heptadiene). Hereinafter this compound will be referred to as a monomer A.

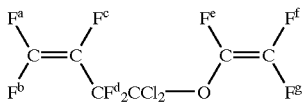

$^{19}$F-NMR (based on CDCl$_3$, CFCl$_3$) δ ppm; −111.3 (F$^a$, J$_{ab}$=83 Hz, J$_{ac}$=65 Hz), −115.6 (F$^b$, J$_{bc}$=111 Hz), −140.2 (F$^c$), −115.5 F$^d$), −183.6 (F$^e$, J$_{ef}$=39 Hz, J$_{eg}$=118 Hz), −83.9 (F$^f$, J$_{fg}$=50 Hz), −97.3 (F$^g$).

EXAMPLE 4

Synthesis of $CF_2$=$CFCF_2CFClOCF$=$CF_2$:
Synthesis of Compound Represented by the Formula 1 from Compound (h)

Into a 500 ml four-necked flask equipped with a stirrer, a reflux condenser and a dropping funnel, 120 g (1.84 mol) of zinc was introduced, and 200 ml of dimethylformamide was introduced thereinto in an atmosphere of an inert gas. Then, the pressure in the system was reduced to 4 kPa, and the internal temperature was adjusted to from 50 to 55° C., and 100 g (0.23 mol) of $CF_2ClCFClCF_2CFClOCFClCF_2Cl$ was dropwise added thereto gradually by the dropping funnel, and the resulting product was quickly taken out by distillation during the reaction. Then, the crude product was purified to obtain 39 g (yield 60%) of pure $CF_2$=$CFCF_2CFClOCF$=$CF_2$ (4-chloro-1,1,2,4,5,5,6,7,7-nonafluoro-3-oxa-1,6-heptadiene). Hereinafter this compound will be referred to as a monomer B.

IR: 1785 cm$^{-1}$ ($CF_2$=CF—), 1835 cm$^{-1}$ ($CF_2$=CFO—); b.p.: 61° C./33 kPa;

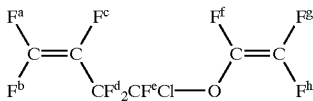

$^{19}$F-NMR (based on CDCl$_3$, CFCl$_3$) δ ppm; −114.9 (F$^a$, J$_{ab}$=83 Hz, J$_{ac}$=65 Hz), −112.3 (F$^b$, J$_{bc}$=111 Hz, J$_{bd}$=6 Hz), −135.3 (F$^c$, J$_{cd}$=10 Hz), −74.9 (F$^d$), −117.3 (F$^e$, J$_{ef}$=14 Hz, J$_{eg}$=6 Hz, J$_{eh}$=27 Hz), −188.2 (F$^f$, J$_{fg}$=39 Hz, J$_{fh}$=118 Hz), −89.1 (F$^g$, J$_{gh}$=50 Hz), −105.4 (F$^h$)

EXAMPLE 5

Polymerization of Monomer A

Into a 100 ml stainless steel autoclave, 50 g of trichlorotrifluoroethane, 30 g (0.097 mol) of the monomer A and 0.1 g (4.85×10$^{-4}$ mol) of diisopropyl peroxydicarbonate were introduced. This autoclave was heated at 50° C. for 3 days with stirring, then the autoclave was opened, followed by after-treatment with methanol. The polymer thus obtained was taken out, and the solvent and the remaining monomer were distilled off under reduced pressure to obtain 29 g of a colorless and transparent polymer. The yield of the obtained polymer was 96%. With respect to the molecular weight of this polymer as calculated as polymethyl methacrylate by gel permeation chromatography (GPC) using a dichloropentafluoropropane solvent (hereinafter referred to as R225) (the same applies to the following molecular weight measurements), the number average molecular weight (Mn) was 123,000 and the weight average molecular weight (Mw) was 42,500.

Of a film prepared by press-molding the polymer, the refractive index measured by an Abbe refractometer was 1.40, and the glass transition temperature measured by a differential scanning calorimeter (DSC) was 168° C. The tensile properties of the polymer were measured, whereupon the elastic modulus was 1,690 MPa, the stress at yield was 50 MPa, and the yield elongation in tension was 3.6%.

The infrared absorption spectrum of the polymer was measured, whereupon an absorption at 1,785 cm$^{-1}$ assigned to $CF_2$=CF— and an absorption at 1,835 cm$^{-1}$ assigned to $CF_2$=CFO—, shown in the spectrum of the monomer, disappeared. This polymer had no pendant double bond, no crosslinking reaction took place, and the polymer completely dissolved in R225 even if the reaction efficiency was high, and accordingly the polymer was found to be a cyclic polymer. Further, by $^{19}$F-NMR analysis, the polymer was found to be a polymer having repeating units of the following structure:

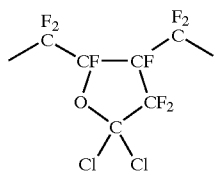

EXAMPLE 6-1

Synthesis of an Oligomer of Monomer A

Into a 100 ml stainless steel autoclave, 30 g of carbon tetrachloride, 60 g (0.194 mol) of the monomer A, 13 g (0.093 mol) of sulfuryl chloride and 0.62 g (2.98×10$^{-3}$ mol) of diisopropyl peroxydicarbonate were introduced. The autoclave was heated at 50° C. for 1 day and at 60° C. for 2 hours with stirring, then the autoclave was opened, and the reaction liquid was washed with a saturated sodium hydrogencarbonate aqueous solution and a saturated sodium chloride aqueous solution. The resulting oligomer was sedimented by centrifugal separation, and the supernatant fluid was removed. Then, the transparent and colorless oligomer thus obtained was batched off into fractions having about the same molecular weights by distillation. The yield of the oligomer obtained was 85%. The molecular weight as estimated by size exclusion chromatography was 1,800 at highest. Hereinafter this oligomer will be referred to as an oligomer A.

EXAMPLE 6-2

Mixing of Oligomer A and Polymer X 750 g of perfluoro(butenyl vinyl ether) (hereinafter referred to as PBVE), 4 kg of deionized water, 260 g of methanol and 3.7 g of diisopropyl peroxydicarbonate were put in a glass flask having an internal volume of 5 l. The atmosphere in the flask was replaced by nitrogen, and suspension polymerization was carried out at 40° C. for 22 hours to obtain 690 g of a polymer having a number average molecular weight of about 5×10$^4$. This polymer was treated in an atmosphere of a fluorine/nitrogen mixed gas (fluorine gas concentration 20 vol %) at 250° C. for 5 hours to obtain a polymer having a good light transmittance and thermal stability (hereinafter referred to as a polymer X).

The polymer X had an intrinsic viscosity [η] of 0.3 dl/g in perfluoro(2-butyltetrahydrofuran) (hereinafter referred to as PBTHF) at 30° C. The polymer X had a glass transition point Tg of 108° C., and was a tough transparent vitreous polymer at room temperature. Further, its refractive index was 1.342.

Relative to 8.4 parts by mass of the polymer X, 1.6 parts by mass of the above oligomer A was dissolved in PBTHF to prepare a fluorine-containing resin composition consisting of a solution having a solid content concentration of 10 mass %. This solution was casted on a glass plate, followed by drying to obtain a film having a thickness of 20 μm. The optical transmittance through this film was measured, whereupon the transmittance of visible light ray having a wavelength of from 350 to 700 nm was at least 90%, and accordingly the fluorine-containing resin composition was found to be a uniform composition without light scattering derived from phase separation.

The content of the oligomer A in the film was 15.0 mass %, and the refractive index of the film was 1.357. Further, the film had a Tg of 80° C.

EXAMPLE 6-3

Production of Optical Fiber

An optical fiber was produced in accordance with a method as disclosed in JP-A-8-5848 using the polymer X (the same as a polymer of PBVE as disclosed in JP-A-8-5848) and the oligomer A (substitute for an oligomer of chlorotrifluoroethylene as disclosed in JP-A-8-5848).

A mixture of the polymer X and the above oligomer A (15.0 mass % of the oligomer A was contained in the mixture) was charged into a glass sealed tube, followed by melt molding at 250° C. to obtain a uniform cylindrical molded product (hereinafter referred to as a molded product (a)). The molded product (a) had a refractive index of 1.357 and a Tg of 80° C.

Then, a cylindrical tube consisting of the polymer X alone was prepared by melt molding, and the molded product (a) was inserted into the hollow part of the cylindrical tube, followed by heating to 200° C. for accretion to obtain a preform. This preform was melt-spun at 240° C. to obtain an optical fiber of which the refractive index gradually decreased from the center portion toward the periphery. The light transmission properties of the obtained optical fiber were 105 dB/km at 650 nm, 45 dB/km at 850 nm and 32 dB/km at 1,300 nm, and the obtained optical fiber was confirmed to be capable of transmitting light in the visible region to the infrared region well.

This optical fiber was preserved in an oven of 60° C. for 10,000 hours and taken out, and then its refractive index distribution was measured by an Interphako interference microscope and compared with the refractive index distribution before the preservation, whereupon no change was observed. Further, the bandwidth was measured by a pulse method to evaluate the transmission properties. After the preservation of the optical fiber at 60° C. for 10,000 hours, the bandwidth was measured, whereupon it was 280 MHz·km before and after the preservation, and no decrease in bandwidth took place, and accordingly the optical fiber was confirmed to be excellent in heat resistance.

EXAMPLE 7

Polymerization of Monomer B 5 g of the monomer B and 12.5 mg of diisopropyl peroxydicarbonate were put in a glass ampul, frozen in liquid nitrogen, subjected to vacuum degassing and sealed. The glass ampul was heated in an oven of 40° C. for 20 hours, then the solidified content was taken off and dried at 200° C. for 1 hour. The yield of the obtained polymer was 80%. A part of the polymer was dissolved in R225 to measure the intrinsic viscosity, whereupon it was 0.20 dl/g. With respect to the molecular weight of the polymer, the number average molecular weight (Mn) was 121,500, and the weight average molecular weight (Mw) was 44,500.

Of a film prepared by press molding of the polymer, the refractive index as measured by an Abbe refractometer was 1.37 and Tg as measured by a differential scanning calorimeter (DSC) was 126° C. The tensile properties of the polymer were measured, whereupon the elastic modulus was 1,700 MPa, the stress at yield was 50 MPa, and the yield elongation in tension was 3.8%.

The infrared absorption spectrum of the polymer was measured, whereupon an absorption at 1,785 cm$^{-1}$ assigned to $CF_2$=CF— and an absorption at 1,835 cm$^{-1}$ assigned to $CF_2$=CFO— shown in the spectrum of the monomer disappeared.

This polymer had no pendant double bond, no crosslinking reaction took place, and the polymer was completely dissolved in R225 even if the reaction efficiency was high, and accordingly the polymer was found to be a cyclic polymer. Further, by $^{19}$F-NMR analysis, the polymer was found to be a polymer having repeating units of the following structure.

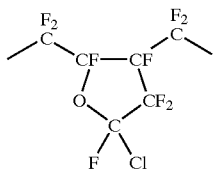

EXAMPLE 8-1

Polymerization of Monomer B 5 g of the monomer B and 12.5 mg of perfluorobenzoyl peroxide were put in a glass ampul, frozen in liquid nitrogen, subjected to vacuum degassing and sealed. The ampul was heated in an oven of 70° C. for 20 hours, and the solidified content was taken off and dried under vacuum at 100° C. for 10 hours. The yield of the obtained polymer was 98%. With respect to the molecular weight of the polymer, the number average molecular weight (Mn) was 132,000 and the weight average molecular weight (Mw) was 51,500. Hereinafter this polymer will be referred to as a polymer B.

Of the obtained stick polymer B, the scattering light intensity of a He—Ne laser light having a wavelength of 633 nm was measured by using a light scattering spectrophotometer to calculate scattering loss, whereupon it was 45 dB/km. Namely, it was found that the polymer B was extremely excellent in transparency, and is useful as optical resin materials for e.g. optical fibers or optical waveguides.

EXAMPLE 8-2

Mixing of Polymer B and Perfluoro(2,4,6-triphenyl-1,3,5-triazine

In the same manner as in Example 6-2, perfluoro(2,4,6-triphenyl-1,3,5-triazine (hereinafter referred to as F triazine) and the polymer B were mixed to obtain a film having a thickness of 20 $\mu$m. The optical transmittance through the film was measured, whereupon the transmittance of visible light ray having a wavelength of from 350 to 700 nm was at least 90%, and accordingly, it was found that the fluorine-containing resin composition was a uniform composition without no light scattering derived from phase separation.

The content of F triazine in the film was 6.0 mass %, and the refractive index of the film was 1.358. Further, this film had a Tg of 92° C.

EXAMPLE 8-3

Production of Optical Fiber

In the same manner as in Example 6-3, a cylindrical uniform molded product (hereinafter referred to as a molded product b) was obtained by using the polymer B and F triazine. The molded product b had a refractive index of 1.358 and a Tg of 92° C.

Then, in the same manner as in Example 6-3, an optical fiber of which the refractive index gradually decreased from the center portion toward the periphery was obtained. The light transmission properties of the obtained optical fiber were 101 dB/km at 650 nm, 40 dB/km at 850 nm and 26 dB/km at 1,300 nm, and it was confirmed that the optical fiber is capable of transmitting light in the visible light region to the infrared light region well.

This optical fiber was preserved in an oven of 60° C. for 10,000 hours and taken out, and then its refractive index distribution was measured by an Interphako interference microscope and compared with the refractive index distribution before the preservation, whereupon no change was observed. Further, the bandwidth was measured by a pulse method to evaluate the transmission properties. After the preservation of the optical fiber at 60° C. for 10,000 hours, the bandwidth was measured, whereupon it was 280 MHz·km before and after the preservation, and no decrease in bandwidth took place, and accordingly the optical fiber was confirmed to be excellent in heat resistance.

EXAMPLE 9

Synthesis of Oligomer of the Monomer B

In the same manner as in Example 6, an oligomer of the monomer B could be obtained. The yield of the oligomer was 80%. The molecular weight as estimated by size exclusion chromatography was 2,000 at highest. Hereinafter this oligomer will be referred to as an oligomer B.

EXAMPLE 9-2

Mixing of Polymer X and Oligomer B

In the same manner as in Example 6-2, the above oligomer B and the polymer X were mixed to obtain a film having a thickness of 20 $\mu$m. The optical transmittance through the film was measured, whereupon the transmittance of visible light ray having a wavelength of from 350 to 700 nm was at least 90%, and accordingly the fluorine-containing resin composition was found to be a uniform composition without light scattering derived from phase separation.

The content of the oligomer B in the film was 14.5 mass %, and the refractive index of the film was 1.350. Further, the film had a Tg of 70° C.

EXAMPLE 9-3

Production of Optical Fiber

In the same manner as in Example 6-3, a cylindrical uniform molded product (hereinafter referred to as a molded product b=) was obtained by using the polymer X and the oligomer B. The molded product b' had a refractive index of 1.350 and a Tg of 70° C.

Then, in the same manner as in Example 6-3, an optical fiber of which the refractive index gradually decreased from the center portion toward the periphery was obtained. The light transmission properties of the obtained optical fiber were 103 dB/km at 650 nm, 42 dB/km at 850 nm and 28 dB/km at 1,300 nm, and it was confirmed that the optical fiber is capable of transmitting light in the visible light region to the infrared light region well.

This optical fiber was preserved in an oven of 60° C. for 10,000 hours and taken out, and then its refractive index distribution was measured by an Interphako interference microscope and compared with the refractive index distribution before the preservation, whereupon no change was observed. Further, the bandwidth was measured by a pulse method to evaluate the transmission properties. After the preservation of the optical fiber at 60° C. for 10,000 hours, the bandwidth was measured, whereupon it was 280 MHz·km before and after the preservation, and no decrease in bandwidth took place, and accordingly the optical fiber was confirmed to be excellent in heat resistance.

EXAMPLE 10

Copolymerization of Monomer B and Tetrafluoroethylene

Into an autoclave of 200 ml, 80 ml of R225, 5 g (17 mmol) of the monomer B and 0.025 g of perfluorobenzoyl peroxide were introduced. The autoclave was vacuumized by a vacuum pump under cooling with liquid nitrogen, then the vacuum pump was disconnected to recover normal pressure, and this operation was repeatedly carried out three times. Then, the internal temperature of the autoclave was recovered to room temperature, and 32 g (320 mmol) of tetrafluoroethylene was introduced. Then, the autoclave was heated until the internal temperature became 70° C., and polymerization was carried out for 3 hours. Then, the remaining tetrafluoroethylene was purged, and the remaining monomer was distilled off under reduced pressure to obtain 25 g of a white polymer (yield 67%). The structure of the obtained polymer was analyzed, whereupon the polymer was found to be a polymer of tetrafluoroethylene containing 2 mol % of units formed by cyclic polymerization of the monomer B.

The fluorine-containing diene of the present invention is a novel compound useful as a fluorine-containing monomer, and undergoes cyclic polymerization to form a polymer having a fluorine-containing alicyclic structure. This polymer has a high transparency and is useful as an optical resin material.

What is claimed is:

1. A polymer which contains monomer units formed by polymerization of a fluorine-containing diene $$CF_2=CF(CF_2)_nCXYOCF=CF_2 \qquad \text{Formula 1}$$

wherein X and Y are hydrogen and chlorine, hydrogen and bromine, hydrogen and iodine, fluorine and chlorine, fluorine and bromine, fluorine and iodine, chlorine and bromine, chlorine and iodine, bromine and bromine, bromine and iodine or iodine and iodine and n is an integer of from 1 to 3.

2. The polymer according to claim 1, wherein the monomer units are formed by cyclic polymerization of the fluorine-containing diene.

3. The polymer of claim 1, wherein X and Y are fluorine and chlorine and n is an integer of from 1 to 3.

4. The polymer according to claim 3, wherein the monomer units are formed by cyclic polymerization of the fluorine-containing diene.

5. A copolymer which contains monomer units formed by polymerization of a fluorine-containing diene, $$CF_2=CF(CF_2)_nCXYOCF=CF_2 \qquad \text{Formula 1}$$

wherein X and Y are hydrogen and chlorine, hydrogen and bromine, hydrogen and iodine, fluorine and chlorine, fluorine and bromine, fluorine and iodine, chlorine and bromine, chlorine and iodine, bromine and bromine, bromine and iodine or iodine and iodine and n is an integer of from 1 to 3 and contains monomer units formed by polymerization of at least one monomer selected from ethylene, tetrafluoroethylene, perfluoro(alkyl vinyl ether), perfluoro(butenyl vinyl ether), perfluoro(allyl vinyl ether) and perfluoro(2,2-dimethyl-1,3-dioxole).

6. A low molecular weight polymer (oligomer) which contains monomer units formed by polymerization of a fluorine-containing diene $$CF_2=CF(CF_2)_nCXYOCF=CF_2 \qquad \text{Formula 1}$$

wherein X and Y are hydrogen and chlorine, hydrogen and bromine, hydrogen and iodine, fluorine and chlorine, fluorine and bromine, fluorine and iodine, chlorine and bromine, chlorine and iodine, bromine and bromine, bromine and iodine or iodine and iodine and n is an integer of from 1 to 3.

7. The copolymer of claim 5, wherein the fluorine-containing diene is 4-chloro- 1,1,2,4,5,5,6,7,7-nonafluoro-3-oxa- 1,6-heptadiene and monomer units are tetrafluoroethylene.

8. The polymer of claim 1, wherein said fluorine-containing diene is 4-chloro- 1,1,2,4,5,5,6,7,7-nonafluoro-3-oxa- 1,6-heptadiene ($CF_2=CFCF_2CClFOCF=CF_2$).

* * * * *